Figure 1:
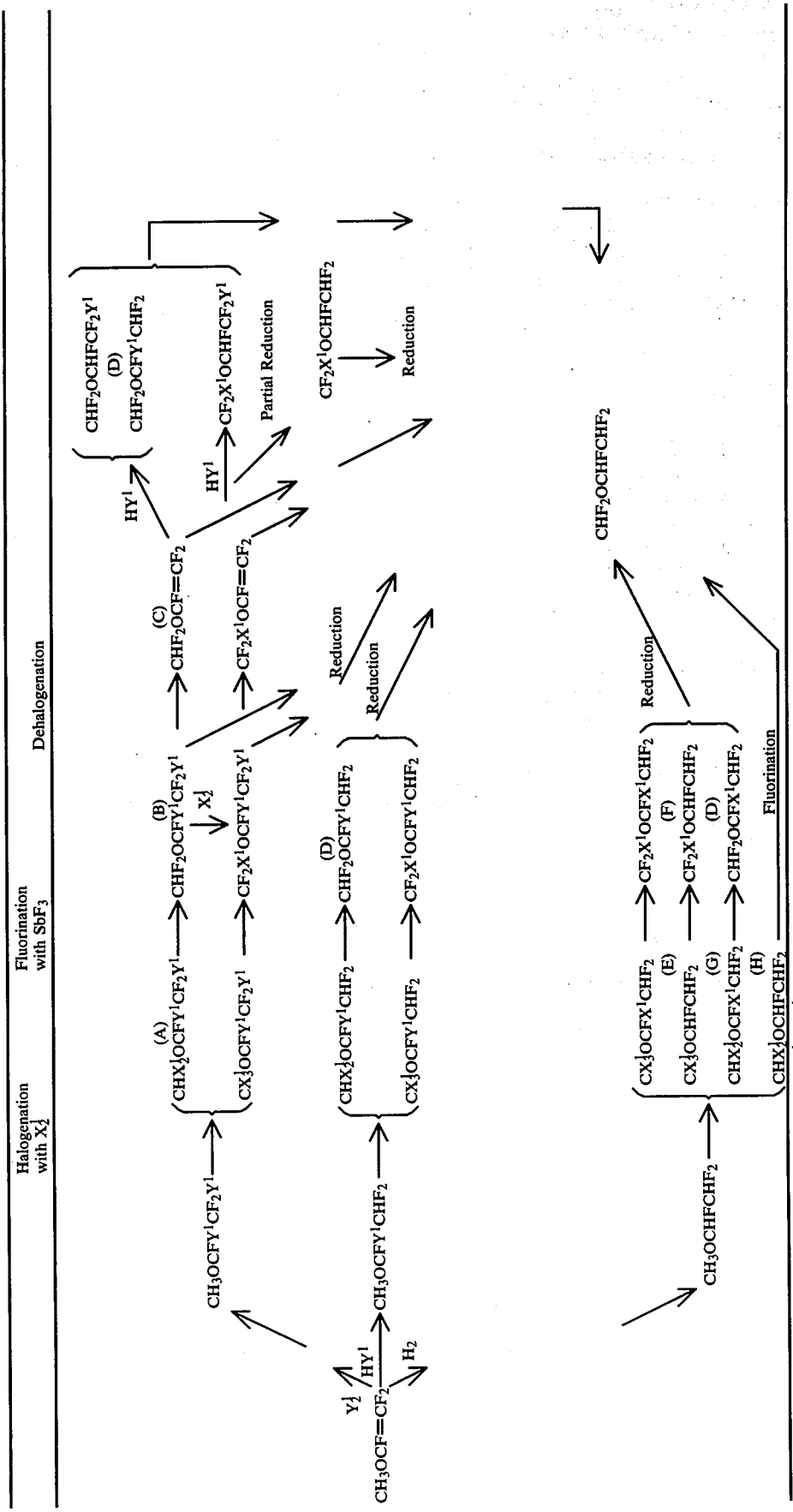

United States Patent [19]

Bell et al.

[11] 4,149,018

[45] Apr. 10, 1979

[54] COMPOUND CHCl$_2$-O-CHF-CHF$_2$

[75] Inventors: William Bell; Keith Pearson; Richard W. Rendell, all of Macclesfield, England

[73] Assignee: Imperial Chemical Industries Limited, London, England

[21] Appl. No.: 875,546

[22] Filed: Feb. 6, 1978

Related U.S. Application Data

[62] Division of Ser. No. 747,996, Dec. 6, 1976, abandoned.

[30] Foreign Application Priority Data

Dec. 5, 1975 [GB] United Kingdom ............... 50040/75

[51] Int. Cl.$^2$ ..................... C07C 43/12; C07C 43/02; A61K 31/075
[52] U.S. Cl. .................................. 568/684; 568/685; 568/683; 424/342
[58] Field of Search ..................................... 260/614 F

[56] References Cited

U.S. PATENT DOCUMENTS

| | | | |
|---|---|---|---|
| 3,535,425 | 10/1970 | Terrell | 260/614 F X |
| 3,663,715 | 5/1972 | Terrell | 260/614 F X |

FOREIGN PATENT DOCUMENTS

2,361,058  6/1975  Fed. Rep. of Germany ....... 260/614 F

*Primary Examiner*—Howard T. Mars
*Attorney, Agent, or Firm*—Cushman, Darby & Cushman

[57] ABSTRACT

A process for the manufacture of the anaesthetic compound CHF$_2$—O—CHF—CHF$_2$ which comprises the reduction of a mono, di- or tri-chlorinated or brominated derivative of the above compound, or the replacement by fluorine of one or more hydrogen, chlorine or bromine atoms in a less-fluorinated derivative of the above compound.

1 Claim, No Drawings

COMPOUND CHCL$_2$-O-CHF-CHF$_2$

This is a division, of application Ser. No. 747,996 filed Dec. 6, 1976, now abandoned.

This invention relates to a chemical process and more particularly it relates to a process for the manufacture of the compound difluoromethyl 1,2,2-trifluoroethyl ether, which has the formula CHF$_2$—O—CHF—CHF$_2$.

This compound has been described as a by-product obtained during the fluorination of 1,4-dioxan over cobalt trifluoride, by Burdon and Parsons in "Tetrahedron" 1971, 27, 4533 to 4551, but the yield (less than 6%) obtained was so small and the separation so complex that this process is impractical for the commercial production of the compound. Furthermore a process for the manufacture of the compound by the fluorination of ethyl methyl ether over cobalt trifluoride has been described by Brandwood et alia in the Journal of Fluorine Chemistry, 1975, 5, 521 to 535, but the yield is less than 1% and it is not practical to separate this amount from the major products of this fluorination. A second process described in this latter publication, the further fluorination over cobalt trifluoride of monofluoromethyl 1,2,2-trifluoroethyl ether at higher temperature, is also inconvenient for the commercial production of the compound.

We have now found, and herein lies our invention, that difluoromethyl 1,2,2-trifluoroethyl ether may conveniently be obtained in commercially attractive yields from the readily available tetrafluoroethylene by a number of processes.

According to the invention there is provided a process for the manufacture of difluoromethyl 1,2,2-trifluoroethyl ether which comprises either the reduction of a compound of the formula:

CF$_2$X—O—CFY—CF$_2$Z wherein X is hydrogen, chlorine or bromine, and wherein either Y and Z, which may be the same or different, each is hydrogen, chlorine or bromine, provided that X, Y and Z are not all hydrogen, or wherein Y and Z are joined together to form an olefinic bond between the two carbon atoms; or the fluorination of a compound of the formula:

CHX$^2$X$^3$—O—CHY$^2$—CHZ$^1$Z$^2$ wherein X$^2$, X$^3$, Z$^1$ and Z$^2$, which may be the same or different, each is fluorine, chlorine or bromine and wherein Y$^1$ is hydrogen, fluorine, chlorine or bromine, provided that X$^2$, X$^3$, Y$^1$, Z$^1$ and Z$^2$ are not all fluorine.

The reduction may be carried out by means of hydrogen and a catalyst, for example a palladium catalyst, particularly an 0.5% or 5% palladium-on-charoal catalyst, and it may be carried out at a temperature appropriate to the reaction to be carried out, for example at a temperature of up to 250° C. Alternatively, the reduction may be carried out by non-catalytic means, for example by means of hydrogen provided by a dissolving metal, for example by use of sodium or zinc dissolving in an alcohol, for example methanol, ethanol or isopropanol, or by use of a complex metal hydride, for example lithium aluminum hydride or sodium borohydride, in an appropriate solvent, for example diglyme.

The various starting materials may be obtained, as shown in FIG. 1, by a series of reactions starting from methyl 1,2,2-trifluorovinyl ether, which is itself conveniently obtained from tetrafluoroethylene as follows:

CF$_2$=CF$_2$+NaOCH$_3$→CH$_3$O—CF=CF$_2$

It is to be understood that in the scheme shown in FIG. 1 two of X, Y and Z may sometimes be the same halogen atom, in which case the same symbol (X$^1$ or Y$^1$) is used in both positions.

Some of the intermediate compounds described in FIG. 1 are novel compounds. In particular, the compounds of the following formulae are novel and are particularly exemplified herein, and these form further features of the invention:

| | | |
|---|---|---|
| CHCl$_2$—O—CFCl—CF$_2$Cl | | (A) |
| CHF$_2$—O—CFCl—CF$_2$Cl | | (B) |
| CHF$_2$—O—CF=CF$_2$ | | (C) |
| CHF$_2$—O—CFCl—CHF$_2$ | | (D) |
| CCl$_3$—O—CHF—CHF$_2$ | | (E) |
| CF$_2$Cl—O—CHF—CHF$_2$ | | (F) |
| CHCl$_2$—O—CFCl—CHF$_2$ | | (G) |
| and | CHCl$_2$—O—CHF—CHF$_2$ | (H) |

The fluorination process of the invention may be carried out using a conventional fluorinating agent Thus, for example, a suitable fluorinating agent which may be used to replace a chlorine or bromine atom $X^2$ or $X^3$ by fluorine is, for example, antimony trifluoride. $X^2$ and $X^3$ are preferably both chlorine atoms. A suitable fluorinating agent which may be used to replace a chlorine or bromine atom $Y^2$, $Z^1$ or $Z^2$ by fluorine is, for example, mercuric fluoride. $Y^2$, $Z^1$ and $Z^2$ are preferable all chlorine atoms. A suitable fluorinating agent which may be used to replace the hydrogen atom $Y^2$ by fluorine is, for example, chlorine trifluoride or bromine trifluoride.

The starting material of the formula $CHF_2-O-CHY^2CHF_2$ wherein $Y^2$ is hydrogen or chlorine is a known compound (Journal of Medicinal Chemistry, 1971, 14, 517 to 519).

The difluoromethyl 1,2,2-trifluoroethyl ether possesses valuable anaesthetic properties and may be used in anaesthetic compositions.

The invention is illustrated but not limited by the following Examples:

EXAMPLE 1

A stream of hydrogen is passed at the rate of 750 ml. per minute through 1,2-dichloro-1,2,2-trifluoroethyl difluoromethyl ether (48 g.) and the gaseous mixture thus obtained is passed through a horizontal tube, 60 cm. long and 7.5 cm. in diameter, which contains a 5% palladium-on-charcoal catalyst (20 g.) heated to a temperature of between 200 and 250° C. The process is continued until all of the ether has been carried over the catalyst. The gases leaving the tube are passed into a vessel cooled with solid carbon dioxide in acetone. The collected liquid is fractionally distilled and there is thus obtained difluoromethyl 1,2,2-trifluoroethyl ether (19 g.), b.p. 53°-54° C.

The 1,2-dichloro-1,2,2-trifluoroethyl difluoromethyl ether used as starting material may be obtained as follows:

Chlorine gas is passed through 1,2-dichloro-1,2,2-trifluoroethyl methyl ether (68 g.) which is contained in a 50 ml. radiation cell fitted with a condenser and a solid carbon dioxide in acetone trap, and which is irradiated by means of a Hanovia medium pressure lamp. An exothermic reaction takes place, the internal temperature rising to 50° C. When the weight of the reaction mixture has increased to 99 g., indicating replacement of two atoms of hydrogen by two atoms of chlorine, the reaction is stopped and the reaction mixture fractionally distilled. There is thus obtained dichloromethyl 1,2-dichloro-1,2,2-trifluoroethyl ether, b.p. 127° C.

The above material (48 g.) is added slowly to antimony trifluoride (35.8 g.) which is stirred at 90° C., and the product which distils from the reaction is collected in a vessel cooled by solid carbon dioxide. The product is fractionally distilled and there is thus obtained 1,2-dichloro-1,2,2-trifluoroethyl difluoromethyl ether, b.p. 61°-61.5° C.

EXAMPLE 2

A stream of hydrogen is passed at the rate of 750 ml. per minute over the surface of difluoromethyl 1,2,2-trifluorovinyl ether (25.4 g.) and the gaseous mixture thus obtained is passed through a horizontal tube, 50 cm. long and 2.5 cm. in diameter, which contains a 5% palladium-on-charcoal catalyst (40 g.) supported on small porcelain cylinders (100 g.) and heated to a temperature of 60° C. The process is continued until all of the ether has been carried over the catalyst. The gases leaving the tube are passed into a vessel cooled with solid carbon dioxide in acetone. The collected liquid (15.6 g.) is fractionally distilled, some starting material (8.5 g.) being recovered, and there is thus obtained difluoromethyl 1,2,2-trifluoromethyl ether, b.p. 53°-54° C., in 40% yield based on the vinyl ether consumed.

The difluoromethyl 1,2,2-trifluorovinyl ether used as starting material may be obtained as follows:

1,2-Dichloro-1,2,2-trifluoroethyl difluoromethyl ether (50 g.) is added dropwise during 30 minutes to a stirred suspension of zinc dust (25 g.) and zinc chloride (1.65 g.) in dimethylsulphoxide (125 ml.) which is maintained at 110° C. The volatile gases which distil out of the reaction mixture are condensed in a trap cooled with solid carbon dioxide in acetone. The collected liquid is fractionally distilled and there is thus obtained difluoromethyl 1,2,2-trifluorovinyl ether, b.p. 10.5°-11° C. (25.4 g.).

EXAMPLE 3

A stream of hydrogen at the rate of 500-600 ml. per minute is passed over difluoromethyl 1,2,2-trifluorovinyl ether (50.4 g.) which is cooled to −5° C. The gaseous mixture thus obtained is passed through a vertical tube, 45 cm. long and 2.5 cm. in diameter, which contains 80 g. of an 0.5% palladium-on-charcoal catalyst heated at 153° C. The gases leaving the tube are passed into a vessel cooled with solid carbon dioxide in acetone. The collected liquid (36 g.) is washed with water and then with saturated aqueous sodium bicarbonate solution, dried over magnesium sulphate and then fractionally distilled. there is thus obtained difluoromethyl 1,2,2-trifluoroethyl ether (21.5 g.), b.p. 53°-54° C.

EXAMPLE 4

A stream of hydrogen is passed at the rate of 500 ml. per minute through 1-chloro-1,2,2-trifluoroethyl difluoromethyl ether (5.7 g.) and the gaseous mixture thus obtained is passed through a vertical tube, 45 cm. long and 2.5 cm in diameter, which contains an 0.56% palladium-on-charcoal catalyst (80 g.) heated at 240° C. The gases leaving the tube are passed into a vessel cooled with solid carbon dioxide in acetone. The collected liquid is poured onto ice-water, separated from the water, dried over magnesium sulphate and fractionally distilled. There is thus obtained difluoromethyl 1,2,2-trifluoroethyl ether, b.p. 53°-54° C., in 45% yield.

The 1-chloro-1,2,2-trifluoroethyl difluoromethyl ether used as starting material may be obtained as follows:

A stream of hydrogen chloride is passed at the rate of 500 ml. per minute over difluoromethyl 1,2,2-trifluorovinyl ether (53 g.) which is cooled to −6° C., and the gaseous mixture thus obtained is passed through a vertical tube, 45 cm. long and 2.5 cm. in diameter, which contains a catalyst consisting of a 4:1 weight by weight mixture of granular carbon (10-18 mesh) and calcium sulphate (8 mesh) heated at 186° C. The reaction is exothermic and the temperature rises to 229° C. The gases leaving the tube are passed into a vessel cooled with solid carbon dioxide in acetone. The collected liquid (42.4 g.) is poured onto ice-water, separated from the water, dried over magnesium sulphate and then fractionally distilled. There is thus obtained 1-chloro-1,2,2-trifluoroethyl difluoromethyl ether (4.5 g., b.p. 56° C.), and later fractions of the distillate consist of 2-chloro-1,2,2-trifluoroethyl difluoromethyl ether (17.5 g., b.p. 56° C., used as starting material in Examples 6, 7 and 8) and 1,2-dichloro-1,2,2-trifluoroethyl difluoromethyl ether (7.9 g., b.p. 61°–61.5° C.)

EXAMPLE 5

A mixture of 1-chloro-1,2,2-trifluoroethyl difluoromethyl ether (1.8 g.), zinc (3.5 g.), zinc chloride (0.3 g.) and absolute alcohol (12 ml.) is heated at 150° C. in a sealed, shaken vessel for 24 hours. The reaction mixture is fractionally distilled and the distillate boiling within the range 54°–77° C. (7.0 g.) is collected. This distillate is further fractionally distilled and there is thus obtained difluoromethyl 1,2,2-trifluoroethyl ether, b.p. 53°–54° C., in 40% yield.

EXAMPLE 6

A mixture of 2-chloro-1,2,2-trifluoroethyl difluoromethyl ether (3 g.), zinc powder (6.5 g.), zinc chloride (0.2 g.) and absolute alcohol (10 ml.) is heated at 150° C. in a sealed glass tube for 24 hours. The reaction mixture is then fractionally distilled using a Vigreux distillation column, and the fraction boiling within the range 42°–60° C. is collected. This material is further separated into its constituents by gas-liquid chromatography using a 10% carbowax column, and there is thus obtained difluoromethyl 1,2,2-trifluoroethyl ether.

EXAMPLE 7

Sodium metal (0.46 g.) is gradually added to a stirred mixture of 2-chloro-1,2,2-trifluoroethyl difluoromethyl ether (1.8 g.) and absolute methanol (1.0 ml.), and after the reaction is complete the mixture is filtered and the filtrate is washed with water and dried over molecular sieve 4A. The material thus obtained is separated into its constituents by preparative gas liquid chromatography using a 20% carbowax 20 M column at 75° C., and there is thus obtained difluoromethyl 1,2,2-trifluoroethyl ether.

EXAMPLE 8

A solution of sodium borohydride (0.53 g.) in diglyme (7 ml.) is added gradually during thirty minutes to a stirred mixture of 2-chloro-1,2,2-trifluoroethyl difluoromethyl ether (1.85 g.), water (0.9 ml.) and diglyme (4 ml.) which is maintained at 5° C. Water is then added to the reaction mixture and the lower organic layer is separated, washed with water and dried over molecular sieve 4A. The material thus obtained is separated into its constituent parts by gas-liquid chromatography, and there is thus obtained difluoromethyl 1,2,2-trifluoroethyl ether.

EXAMPLE 9

A stream of hydrogen at the rate of 500–600 ml. per minute is passed through a mixture of 1-bromo-1,2,2-trifluoroethyl difluoromethyl ether (4.2 g.) and 2-bromo-1,2,2-trifluoroethyl difluoromethyl ether (2.0 g.) and the gaseous mixture thus obtained is passed through a vertical tube, 45 cm. long and 2.5 cm. in diameter, which contains 80 g. of an 0.5% palladium-on-charcoal catalyst heated at 240° C. The gases leaving the tube are passed into a vessel cooled with solid carbon dioxide in acetone. the collected liquid is poured onto ice-water and the non-aqueous layer is separated, dried over magnesium sulphate and then fractionally distilled. There is thus obtained difluoromethyl 1,2,2-trifluoroethyl ether, b.p. 53°–54° C., in 40% yield.

The mixture of difluoromethyl 1-bromo-1,2,2-trifluoroethyl ether and difluoromethyl 2-bromo-1,2,2-trifluoroethyl ether used as starting material may be obtained as follows:

A stream of hydrogen bromide is passed at a rate of 500 ml. per minute over difluoromethyl 1,2,2-trifluorovinyl ether (21.3 g.) which is cooled to −8° C., and the gaseous mixture thus obtained passed through a vertical tube, 45 cm. long and 2.5 cm. in diameter, which contains a catalyst consisting of a 4:1 weight by weight mixture of granular carbon (10–18 mesh) and calcium sulphate (8 mesh) heated at 158° C. The reaction is exothermic and the temperature rises to 170° C. after the passage of gases has continued for 20 minutes. The gases leaving the tube are passed into a vessel cooled with solid carbon dioxide in acetone. The collected liquid (15 g.) is poured into ice-water and the organic layer is separated, dried over magnesium sulphate and then fractionally distilled. There is thus obtained a mixture of 1-bromo-1,2,2-trifluoroethyl difluoromethyl ether (7 g.), b.p. 72.5° C., and 2-bromo-1,2,2-trifluoroethyl difluoromethyl ether (3.3 g.), b.p. 72.5°–73° C.

EXAMPLE 10

Chlorine gas is passed through methyl 1,2,2-trifluoroethyl ether (14 g.) which is contained in a glass radiation cell fitted with a condenser and a solid carbon dioxide in acetone trap, and which is cooled in ice-water and irradiated by means of a Hanovia medium pressure lamp, until 17 g. of chlorine have been absorbed. The reaction mixture is distilled and there is thus obtained a mixture containing as main components dichloromethyl 1,2,2-trifluoroethyl ether, trichloromethyl 1,2,2-trifluoroethyl ether and dichloromethyl 1-chloro-1,2,2-trifluoromethyl ether. This mixture is added dropwise to a stirred mixture of antimony trifluoride (20 g.) and antimony pentachloride (1 ml.) which is heated at 105° C., and the product which distils from the reaction having a boiling point within the range 53° to 66° C. is collected. This product is fractionally distilled and there is thus obtained as second fraction difluoromethyl 1,2,2-trifluoroethyl ether, b.p. 53°–54° C., yield 23% based on the methyl trifluoroethyl ether starting material. Another product of the fluorination reaction, which is the first fraction in the distillation, is chlorodifluoromethyl 1,2,2-trifluoroethyl ether, b.p. 46° C. (yield 20%).

The methyl 1,2,2-trifluoroethyl ether used as starting materisl may be obtained as follows:

A stream of hydrogen is passed for 2 hours at the rate of 750 ml. per minute over methyl 1,2,2-trifluorovinyl ether (22 g.) and the gaseous mixture thus obtained is passed down a column, 16 mm. internal diameter, containing a 1% palladium on 4–8 mesh granular charcoal catalyst (24 g.). The gases emerging from the column are condensed in a trap cooled with solid carbon dioxide in acetone. The column is then purged with a stream of nitrogen for 18 hours, and the gases emerging are similarly condensed. The product is distilled and there is thus obtained methyl 1,2,2-trifluoroethyl ether, b.p. 55°–57° C. (yield, 71%).

EXAMPLE 11

A mixture of 1-chloro-2,2-difluoroethyl difluoromethyl ether (5.0 g.) and mercuric fluoride (3.6 g.) is heated at 115° C. in a sealed tube under an atmosphere of nitrogen for 4 hours. The reaction mixture is fractionally distilled and there is thus obtained difluoromethyl 1,2,2-trifluoromethyl ether (1.9 g.), b.p. 53°–54° C.

What we claim is:

1. The compound $CHCl_2-O-CHF-CHF_2$.

* * * * *